United States Patent [19]

Arnaudis

[11] Patent Number: 4,923,976
[45] Date of Patent: May 8, 1990

[54] PROCESS FOR PREPARING SURFACE-ACTIVE GLYCOSIDES AND THE USE OF THE GLYCOSIDES IN COSMETIC, PHARMACEUTICAL AND HOUSEHOLD PRODUCTS

[75] Inventor: Germaine Arnaudis, Castres, France

[73] Assignee: Rohm and Haas S.A., Paris Cedex, France

[21] Appl. No.: 437,508

[22] Filed: Oct. 28, 1982

[51] Int. Cl.$^5$ .................. C07H 1/00; C07G 3/00
[52] U.S. Cl. .................. 536/18.6; 536/120; 536/127; 536/84; 127/70
[58] Field of Search .......... 536/18.6, 127, 84, 111, 536/120; 127/70

[56] References Cited

U.S. PATENT DOCUMENTS

| | | | |
|---|---|---|---|
| 294,531 | 3/1884 | Underhill | 127/70 |
| 2,001,925 | 8/1932 | Thurber | 127/70 |
| 2,356,565 | 8/1944 | Chwala | 536/17.9 |
| 3,737,426 | 6/1973 | Throckmorton et al. | 536/18.6 |
| 3,839,318 | 10/1974 | Mansfield | 536/18.6 |
| 3,842,005 | 10/1974 | Moser et al. | 536/50 |
| 3,931,148 | 1/1976 | Langdon | 536/50 |
| 4,223,129 | 9/1980 | Roth et al. | 536/120 |
| 4,704,453 | 11/1987 | Lorenz et al. | 536/18.6 |
| 4,713,447 | 12/1987 | Letton | 536/18.6 |
| 4,719,272 | 1/1988 | Tsai et al. | 536/17.9 |
| 4,797,478 | 1/1989 | Lebuhn et al. | 536/18.6 |

*Primary Examiner*—Ronald W. Griffin

[57] ABSTRACT

Surface active glycosides are made by reaction of monose or polyose with an alcohol in the presence of an acid catalyst composition containing acid catalyst and reducing agent; the color properties of the glycosodes so made makes them attractive for use in cosmetic, pharmaceutical and household products. Suitable reducing agents include phosphorous, hypophosphorous, sulphurous, hyposulphurous, nitrous and hyponitrous acids. Suitable catalysts include the known etherification catalysts.

6 Claims, No Drawings

PROCESS FOR PREPARING SURFACE-ACTIVE GLYCOSIDES AND THE USE OF THE GLYCOSIDES IN COSMETIC, PHARMACEUTICAL AND HOUSEHOLD PRODUCTS

This invention is concerned with the process of manufacture of glycosides from alcohols and poly and/or mono saccharides and the use of said glycosides in cosmetic, pharmaceutical and household products. Typical products of the reaction are mixtures of substituted monosaccharides and substituted poly-, mostly oligosaccharides, with surface-active and such colour properties as to enable them to be used in cosmetic, pharmaceutical and household products.

The glycosides to which the invention relates are generally a mixture of various monomeric and oligomeric materials and are non-ionic surface active agents which possess:
high foaming power
emulsifying properties
softening and detergent properties.
These products are readily biodegraded.

In this specification we intend the prefix "oligo" to include as many as eleven repeating units. Alkylsaccharides are molecules which have been known for many years, since Fischer described them in 1909, but their method of manufacture, resulting in specific products, was too difficult or too costly for them to be developed industrially. The methods used consisted of:
reacting acetic anhydride with glucose to form glucose pentacetate, then transforming this product to bromo-tetracetate by the action of hydrobromic acid. The reaction of this glucose bromotetracetate with a fatty alcohol in the presence of silver oxide results in glucoside tetracetate which only requires hydrolysis for glucoside to be obtained.
reacting glucose pentacetate, prepared as above, with a fatty alcohol in the presence of zinc chloride, which again results in glucoside tetracetate, again requiring hydrolysis.

In 1965 a process for preparing ethers from glucose fatty alcohols was described in U.S. Pat. No. 3,170,915 (Monsanto). This method consists of reacting a sugar with sodium methylate in dimetyl sulphoxide and making a halogenised paraffin react on the soda derivate obtained.

These processes are too expensive and yield will defined products.

In 1965 Rohm and Haas described in U.S. Pat. No. 3,219,656 a process for manufacturing glucosides by transetherification between a methylglucose and heavier alcohols. In fact, the etherification of sugars by methyl alcohol is readily achieved by the convetional etherification processes and results in a methylglucose which is considerably more stable with regard to heat and oligomerisation than glucose.

The Rohm and Haas process consists of transetherifying this methylglucose using butyl alcohol in order to obtain butyl ether from the glucose which is itself transetherified with the aid of a fatty alcohol, these two reactions being carried out in the presence, as a catalyst, of a cation-exchanging resin of a type such as those described in U.S. Pat. No. 3,037,052 in the name of the same firm. This process, although less expensive, still requires the consecutive elimination of two light alcohols with the cost these two operations entail, and the unavoidable loss of solvent.

In 1974, in U.S. Pat. No. 3,839,318, Rohm and Haas described the preparation of a mixture of mono-substituted mono-saccharide and mono-substituted oligosaccharide obtained by a direct reaction of a fatty alcohol and a monosaccharide in the presence of an excess of alcohol and an acidic catalyst such as sulphuric acid, nitric acid, hydrochloric acid, sulphonic acid, at a temperature of 80° to 130° C.

The reaction conditions are defined very precisely so that the basic monosaccharide is not subjected to too high a level of degradation during the course of condensation.

The excess of fatty alcohol relative to the monosaccharide must be sufficient; the level of excess required becomes greater as the molecular weight of the alcohol increases. A curve is attached to this prior specification showing the minimum excess of fatty alcohol to be used, as a function of the number of carbon atoms contained in the molecule.

This process yields a mixture of glycosides possessing very useful surface-active properties, a high level of stability to salts and alkaline agents, but the colour of the mixture is too deep for it to be used in the cosmetic or pharmaceutical industries, or for formulating products for domestic use, without purification or extensive decoloration with the aid of powerful oxidants.

We have now found a process which is capable of preparing such a mixture of fatty alcohol ethers and mono- and oligo-saccharides which yields a useful surface-active product, and the purity and coloration of which allow it to be used in cosmetic and pharmaceutical products and for the formulation of products for household use without a subsequent decolorisation step.

The advantages of eliminating the decoloration step are not only economic but also from the aspect of the quality of the product, as this decoloration process entails the formation of unstable oxidised products which may later result in modification of the colour or the pH.

This invention relates in particular to glycosides of the structure:

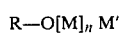

wherein:
n is preferably 0 to 10 but may be much higher, for example such as would result from the reaction of hydrolysed starch or cellulose,
M and M' represent the same or different monose or polyose residues which in the case of M may be a mixture,
R is
(a) a linear paraffinic chain containing 8 to 18 carbon atoms;
(b) a branched primary or secondary hydrocarbon chain containing 8 to 18 carbon atoms; or
(c) a radical of the formula:

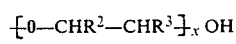

wherein:
x is 1 to 8, and R' is
a linear paraffinic chain;
a branched hydrocarbon chain; or
a monoalkyl or dialkylphenol, and $R^2$ and $R^3$ are either both hydrogen or one is hydrogen and the other is methyl.

In the above "monose" means mono-aldose or mono-ketose According to our invention surface active glycosides are prepared by reacting an alcohol with an aldose or ketose in the presence of an acid catalyst composition comprising an acid catalyst and a reducing agent.

Suitable catalysts are any acid catalysts known to be useful in etherification reactions such as sulphuric acid, hydrochloric acid, nitric acid, sulphonic acid and strong acid cation exchange resins.

Suitable reducing agents include acid reducing agents such as phosphorous hypophosphorous, sulphurous, hyposulphurous, nitrous and hyponitrous acid, which are preferred. These may be used in the form of their salts as long as the overall catalyst plus reducing agent composition remains acid.

The reaction time necessary for etherification depends on such normal factors as the catalyst used, its quantity and the temperature.

The conditions described in U.S. Pat. No. 3,839,318 may appropriately be used in this invention. They generally indicate the optimum and an acceptable balance between quality and the price of the product obtained.

The ratio of fatty alcohol to aldose or ketose lies between 4 to 1 and 1.25 to 1 by mole.

The reaction temperature is preferably 80° to 130° C.

The quantity of catalyst plus reducing agent is preferably 0.03 to 10% of the weight of the charged aldose and/or ketose.

Under these conditions and without significantly modifying the reaction speed it is possible to obtain a less coloured condensation product using the invention than when the reducing agent is absent as in the prior art.

It has been further shown that the addition of a reducing acid to the usual etherification catalyst allows, without modifying the speed of reaction, the quantity of catalyst to be reduced. The speed of reaction obtained by using 0.014 moles of sulfuric acid per mole of glucose can for example be maintained by replacing half of this acid by hypophosphorous acid (0.007 moles).

Furthermore, while it is clearly desirable, whatever the catalyst, to remove the excess alcohol as quickly as possible, so as to minimise the time for which the reaction product is subjected to elevated temperature, it is preferable to effect this removal in the presence of the reducing agent so as to minimise colour deterioration still further.

This elimination of excess alcohol can be accomplished by one of the known methods such as vacuum distillation, molecular distillation and thin film evaporation.

Suitable alcohols include fatty alcohols ($C_{10}$ and above) and they may be linear or branched, primary or secondary. The alcohols may contain in their molecules phenyl, alkylphenyl or alkoxy radicals.

The ketoses and aldoses which may be used in this process may be monoses or polyoses for example suitable monoses include arabinose, galactose, glucose, mannose, ribose and xylose and suitable polyoses include saccharose, maltose, lactose and raffinose, as well as saccharides obtained by hydrolysis of higher polysaccharides such as starch and cellulose.

The glycosides obtained by this process are generally transparent, vitreous solids with a sticky surface. They may be diluted with water so that they can be presented commercially in the form of an aqueous solution.

The following Examples of some embodiments of the invention are give for the purpose of illustration only.

EXAMPLE I

A mixture containing:
732.5 g of an n-octanol and n-decanol 45/55 mixture (5 moles)
360 g of glucose (2 moles)
1.4 g of 98% sulphuric acid (0.014 moles)
1.85 g of 50% hypophosphorous acid (0.014 moles)
is processed for 6 hours at 95° C. in a vacuum at 40 mm of mercury. The solution obtained (in the excess of alcohol) after centrifuging to eliminate approximately 0.5% of non-reacted glucose has a monoalkylglucoside content of 19% and a VCS of 3.

This mixture is neutralised to a pH of 4-6 using caustic soda, and the excess of fatty alcohol is eliminated by vacuum stripping.

The product obtained in a 70% solution in water has a colour of VCS 6, and its aqueous solution at 5% has a pH of 5.

COMPARATIVE TEST A

A product with a composition similar to that of Example 1, prepared according to the process described in U.S. Pat. No. 3,839,318, using the same amounts n-octanol, n-decanol and glucose as in Example 1 with 0.02 moles of sulphuric acid and no hypophosphorous acid yielded a glucoside with a colour of VCS 17 to 18 having been stripped by the same process as in Example 1. The monoglucoside content and the reaction speed are the same in the two cases, although the quantity of sulphuric acid used is two times less in the present example.

EXAMPLE II

A mixture containing:
732.5 g of a 45/55 mixture of n-octanol and n-decanol (5 moles)
360 g of glucose (2 moles)
1.4 g of 98% sulphuric acid (0.014 moles)
3.44 g of 50% hypophosphorous acid (0.026 moles)
is processed under the same operating conditions. The product obtained has a colour of VCS 6 in a 70% solution in water, and its 5% solution in water has a pH of 3.3.

EXAMPLE III

A mixture containing:
732.5 g of a 45/55 mixture of n-octanol and n-decanol (5 moles)
360 g of glucose (2 moles)
1.4 g of 98% sulphuric acid (0.014 moles)
6.88 g of 50% hypophosphorous acid (0.052 moles)
is processed under the same conditions as in Example I.

The 70% solution in water obtained has a colour of VCS 5 and its 5% aqueous solution has a pH of 2.9.

EXAMPLE IV

A mixture containing:
510 g of n-hexanol (5 moles)
360 g of glucose (2 moles)
1.4 g of 98% sulphuric acid (0.014 moles)
1.85 g of 50% hypophosphorous acid (0.014 moles)
is processed according to the process described in Example I.

The product obtained is a mixture of hexylglucose and hexylolisoglucoside with a colour of VCS 5 to 6.

EXAMPLE V

A mixture containing:
732.5 g of a 45/55 mixture of n-octanol and n-decanol (5 moles)
360 g of fructose (2 moles)
1.4 g of 98% sulphuric acid (0.014 moles)
1.85 g of 50% hypophosphorous acid (0.014 moles),
processed according to the process described in Example I, yields a fructoside with a colour of VCS 6 in a 70% aqueous solution.

This product is endowed with the same surface-active properties as the glucose derivative.

EXAMPLE VI

A mixture containing:
790 g of n-decanol (5 moles)
360 g of glucose (2 moles)
4 g of 98% sulphuric acid (0.04 moles)
1.3 g of sodium hypophosphite (0.014 moles),
processed according to the process described in Example I, yields a glucoside with a colour of VDS 6 in a 70% aqueous solution.

EXAMPLE VII

A mixture containing:
732.5 g of a 45/55 mixture of n-octanol and n-decanol (5 moles)
360 g of glucose (2 moles)
1.4 g of sulphuric acid (98%) (0.014 moles) and
1.328 g sodium metabisulphite (0.007 moles)
is processed for 6 hours at 95° C. in a vacuum of 40 mm of mercury.

The reaction product, after neutralisation to a pH of 4 to 6, was treated under vacuum until elimination of excess alcohol. The glucoside obtained had, in 70% aqueous solution, a VCS colour of 6.

EXAMPLE VIII

A mixture containing:
732.5 g of a 45/55 mixture of n-octanol and n-decanol (5 moles)
360 g of glucose (2 moles)
0.7 g of 98% sulphuric acid (0.007 m) and
0.925 g of 50% hypoposphorous acid (0.007 m)
is processed according to the process described in Example 1. The percent solids (vol/vol) in the reacting mixture is measured every hour, the falling value of this percentage indicating progress of the reaction towards completion. The results of these measurements, together with the VCS colour in 70% solution of the product, are given in Table I.

COMPARATIVE EXAMPLES B AND C

Example VIII is repeated except that the sulphuric acid and hypophosphorous acid in the Example are replaced by the indicated amounts of sulphuric acid alone, as given in Table 1.

From the Table it can be seen that the rate of reaction according to the invention was not significantly below the best of the Comparative Examples but the colour was significantly improved.

TABLE 1

| | Experiment: | | |
|---|---|---|---|
| | Comparative Example B | Comparative Example C | Example VIII |
| | mole ratio acid/glucose | | |
| time (hours) | 0.014 H$_2$SO$_4$ | 0.007 H$_2$SO$_4$ | 0.007 H$_2$SO$_4$ 0.007 H$_3$PO$_2$ |
| | Percent solids in the mixture (vol./vol.) | | |
| 1 | 40 | 56 | 44 |
| 2 | 10 | 40 | 34 |
| 3 | 0.5 | 12 | 5 |
| 4 | 0.3 | 6 | 1.5 |
| 5 | 0.2 | 1.2 | 0.7 |
| 6 | 0.1 | 0.5 | 0.3 |
| VCS of product concentrated to 70% aqueous solution | >18 | 14 | 11 |

I claim:

1. A process for the preparation of surface active glycosides having improved color which comprises reacting a C$_8$–C$_{18}$ fatty alcohol with an aldose or ketose in a mole ratio of from 1.25:1 to 4:1 in the presence of from 0.03 to 10% by weight, based on the weight of the aldose or ketose, of an acid catalyst composition comprising an acid catalyst useful in etherification reactions and an acid reducing agent or salt thereof.

2. The process as claimed in claim 1 wherein the aldose or ketose is hyrolyzed starch or cellulose.

3. The process as claimed in claim 1 which is carried out at a temperature of 80° to 130° C.

4. The process as claimed in claim 1 wherein the reducing agent is selected from the group consisting of the free acid form or water-soluble salts of phosphorous, hypophosphorous, sulfurous, hyposulfurous, nitrous and hyponitrous acid and mixtures thereof.

5. The process as claimed in claim 1 wherein fatty alcohol not consumed during the reaction is removed from the reacted mixture in the presence of the reducing agent.

6. The process as claimed in claim 1 wherein the aldose or ketose is selected from the group consisting of arabinose, galactose, glucose, mannose, ribose, xylose, saccharose, maltose, lactose and raffinose.

* * * * *

UNITED STATES PATENT AND TRADEMARK OFFICE
CERTIFICATE OF CORRECTION

PATENT NO. : 4,923,976
DATED : May 8, 1990
INVENTOR(S) : Germaine Arnaudis

It is certified that error appears in the above-identified patent and that said Letters Patent is hereby corrected as shown below: ON TITLE PAGE:

In abstract  Line 5, "glycosodes" should be -- glycosides --

Column 1, line 47, "dimetyl" should be -- dimethyl --

Column 1, line 56 "convetional" should be -- conventional --

Column 2, line 61,  " $[O-CHR^2-CHR^3]_x OH$ "

should be -- $R'[O-CHR^2-CHR^3]_x OH$ --

Column 6, line 39, "hyrolyzed" should be -- hydrolyzed --

Signed and Sealed this

Twenty-second Day of October, 1991

Attest:

HARRY F. MANBECK, JR.

*Attesting Officer*  *Commissioner of Patents and Trademarks*